United States Patent [19]

Bolhofer et al.

[11] 4,220,654

[45] Sep. 2, 1980

[54] CYCLIC IMIDAZOLE CYANOGUANIDINES

[75] Inventors: William A. Bolhofer, Frederick; Edward J. Cragoe, Jr., Lansdale; Jacob M. Hoffman, Jr., North Wales, all of Pa.

[73] Assignee: Merck & Co., Inc., Rahway, N.J.

[21] Appl. No.: 45,545

[22] Filed: Jun. 4, 1979

[51] Int. Cl.$^2$ .................. C07D 233/64; A61U 31/45
[52] U.S. Cl. .................. 424/273 R; 548/336; 548/342; 548/337; 260/325 PH
[58] Field of Search .................. 548/342, 336; 424/273 R

[56] References Cited

U.S. PATENT DOCUMENTS

| | | | |
|---|---|---|---|
| 3,897,444 | 7/1975 | Durant et al. | 548/342 |
| 3,932,443 | 1/1976 | White | 548/342 |
| 3,950,333 | 4/1976 | Durant et al. | 424/256 |
| 3,979,398 | 9/1976 | White | 548/342 |
| 4,000,296 | 12/1976 | Durant et al. | 548/342 |
| 4,038,408 | 7/1977 | Durant et al. | 548/342 |
| 4,049,671 | 9/1977 | Durant et al. | 548/342 |
| 4,083,988 | 4/1978 | Durant et al. | 548/342 |
| 4,093,621 | 6/1978 | Brown et al. | 548/342 |
| 4,098,898 | 7/1978 | Durant et al. | 548/342 |
| 4,109,003 | 8/1978 | Durant et al. | 548/342 |
| 4,112,234 | 9/1978 | Crenshaw et al. | 548/342 |
| 4,128,658 | 12/1978 | Price et al. | 424/285 |

OTHER PUBLICATIONS

Yamanouchi Pharmaceutical Co., Derwent Abstract 75065A/42 and 750654A/42.

*Primary Examiner*—Henry R. Jiles
*Assistant Examiner*—Jane T. Fan
*Attorney, Agent, or Firm*—David L. Rose; Harry E. Westlake

[57] ABSTRACT

There are disclosed novel compounds described as imidazole cyanoguanidines in which the imidazole moiety is connected to the cyanoguanidine moiety through a cyclic group which may optionally contain one or two alkylene linkages. The cyclic groups may be phenyl, cyclohexyl, thienyl and the like. Processes for the preparation of such compounds are also disclosed. The compounds are useful for the suppression of gastric acid secretion in mammals, and compositions for such uses are also disclosed.

12 Claims, No Drawings

CYCLIC IMIDAZOLE CYANOGUANIDINES

BACKGROUND OF THE INVENTION

Imidazolyl cyanoguanidines in which the imidazole and cyanoguanidine are joined through a linear connecting group are known as H-2 receptor inhibitors. See U.S. Pat. No. 3,950,333 to Durant et al. In addition, work has been done on other cyanoguanidines in which a phenyl group is present in the connecting linkage between the imidazole and the cyanoguanidine, however, the connecting group as a whole requires an oxygen or sulfur heteroatom. See Japan Pat. No. 53,103,468 and Derwent Abstract 75064A/42.

SUMMARY OF THE INVENTION

This invention is concerned with imidazole cyanoguanidines wherein the two groups are joined by a connecting group consisting of a cyclic moiety and up to two optional alkylene linkages. The cyclic groups may be phenyl, cyclohexyl, thienyl, tetrahydrothienyl, 13-dithianyl and the like. Thus, it is an object of this invention to describe such compounds. A further object of this invention is to describe processes for the preparation of such compounds. A still further object is to describe the use of such compounds as gastric acid secretion inhibitors in mammals. Further objects will become apparent from a reading of the following description.

DESCRIPTION OF THE INVENTION

The compounds of this invention are best described in the following structural formula:

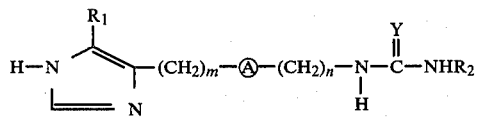

wherein
$R_1$ is hydrogen or methyl;
$R_2$ is loweralkyl;
m and n are independently 0 to 3;
Ⓐ is a cyclic bivalent radical selected from phenylene, cyclohexylene, thienylene, tetrahydrothienylene, and 1,3-dithianylene which may be optionally substituted with a halogen;
Y is oxygen, sulfur, $=NR_3$ or $=CHR_4$ wherein $R_3$ is hydrogen, cyano, loweralkyl, phenyl, loweralkylsulfonyl, or phenylsulfonyl; and
$R_4$ is nitro, phenylsulfonyl, or loweralkyl-sulfonyl.

Preferred compounds of this invention are realized when Y is cyanoimino.

Further preferred compounds of the instant invention are realized when in the above formula:
$R_1$ is methyl;
$R_2$ is methyl;
m and n are independently 0 or 1;
Ⓐ is as defined above; and
Y is cyanoimino.

Further preferred compounds are realized when Ⓐ is phenylene, or cyclohexylene which may be substituted with chlorine.

Still further preferred embodiments are realized when Ⓐ is 1,3-phenylene, chloro-1,3-phenylene, 1,3-cyclohexylene or 1,2-phenylene.

Specific preferred compounds of this invention are:
N-cyano-N'-methyl-N''-(3-[5(4)-methyl-4(5)-imidazolyl]phenyl)guanidine.
N-cyano-N'-methyl-N''-(4-chloro-3-[5(4)-methyl-4(5)-imidazolyl]phenyl)guanidine.
N-cyano-N'-methyl-N''-(cis-3-[5(4)-methyl-4(5)-imidazolyl]cyclohexyl)guanidine.
N-cyano-N'-methyl-N''-(2-[5(4)-methyl-4(5)-imidazolyl]benzyl)guanidine.

In the instant application the term "loweralkyl" is intended to include those alkyl groups, of either a straight or branched chain, having from 1 to 5 carbon atoms. Exemplary of such alkyl groups are methyl, ethyl, propyl, isopropyl, butyl, sec-butyl, tert-butyl, pentyl, and the like.

The term "halogen" is intended to include the halogen atom fluorine, chlorine, bromine and iodine.

The compounds according to the invention readily form physiologically acceptable salts. Such salts include salts with inorganic and organic acids such as hydrochlorides, hydrobromides and sulphates. Particularly useful salts of organic acids are formed with aliphatic mono- or di-carboxylic acids. Examples of such salts are acetates, maleates and fumarates. The compounds may also form hydrates.

The compounds according to the invention can be administered orally, topically or parenterally or by suppository, of which the preferred route is the oral route. They may be used in the form of the base or as a physiologically acceptable salt. They will in general be associated with a pharmaceutically acceptable carrier or diluent, to provide a pharmaceutical composition.

The compounds according to the invention can be administered in combination with other active ingredients, e.g. conventional antihistamines if required. For oral administration the pharmaceutical composition can most conveniently be in the form of capsules or tablets, which may be slow release tablets. The composition may also take the form of a dragee or may be in syrup form. Suitable topical preparation include ointments, lotions, creams, powders and sprays.

A convenient daily dose by the oral route would be of the order of 100 mg. to 1.2 g. per day, in the form of dosage units containing from 20 to 200 mg. per dosage unit. A convenient regimen in the case of a slow release tablet would be twice or three times a day.

Parenteral administration may be by injection at intervals or as a continuous infusion. Injection solutions may contain from 10 to 100 mg./ml. of active ingredient.

For topical application a spray, ointment, cream or lotion may be used. These compositions may contain an effective amount of the active ingredient, for example of the order of 1½ to 2% by weight of the total composition.

The compounds of the present invention may be made by reacting a primary amine of the formula:

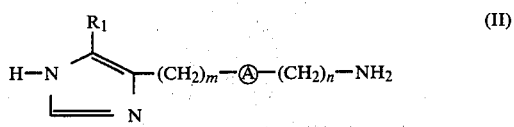

in which $R_1$, m, n, and Ⓐ have the meanings given herein with a compound capable of introducing directly or indirectly the group:

in which $R_2$ and $Y$ have the meanings given herein. Compounds which are capable of introducing the group:

are, isocyanates $R_2NCO$, isothiocyanates $R_2NCS$, or compounds of the formula:

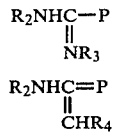

where P is a leaving group. The reaction with the isocyanate or isothiocyanate may be carried out by allowing the amine and isocyanate or isothiocyanate to stand in a solvent such as acetonitrile. The reaction between the amine (II) and:

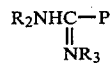

may be carried out in a solvent e.g. ethanol or acetonitrile at ambient or elevated temperatures in the presence of silver nitrate as required. The amine (II) and the compound:

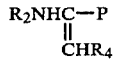

may be stirred in solvents such as ethanol and acetonitrile at room temperature. Where $R_2$ represents hydrogen, alkali metal cyanates and thiocyanates are used. Examples of leaving groups are halogen, thiomethyl, or alkoxy, preferably thiomethyl. The introduction of the group:

may also be effected by first reacting the amine (II) with a compound of the formula:

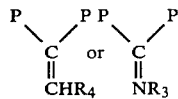

in which P is a leaving group as defined above. This reaction may be effected in a solvent, e.g. ether or acetonitrile at a temperature from ambient to reflux. Treatment of the resulting compound of formula (III):

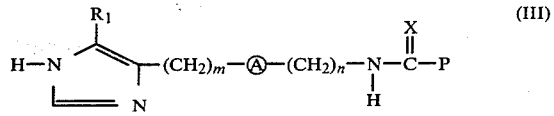

where X represents $=NR_3$ or $=CHR_4$ with a primary amine $R_2NH_2$ at a temperature from ambient to reflux gives the desired end product.

The preferred compounds of this invention wherein Y is a cyanoimino group are prepared according to the following reaction scheme:

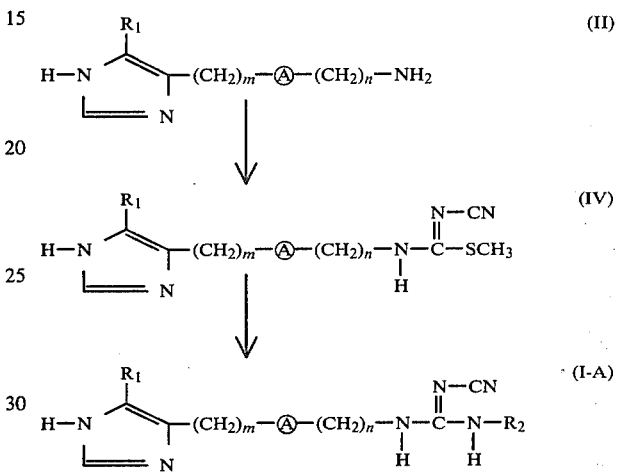

wherein $R_1$, $R_2$, m, n and Ⓐ are as defined above.

In the first step of this reaction sequence the amine starting material (II) is treated with dimethyl cyanodithioimidocarbonate in a suitable solvent, preferably acetonitrile or a lower alcohol, such as ethanol. The reaction may be carried out at about 20° C. to the reflux temperature of the reaction mixture. The reaction is substantially complete in about 1 hour to several days. It is preferred to stir the reaction mixture overnight at about room temperature.

The next step of this reaction sequence involves the displacement of the methylthio group of Compound IV by a loweralkylamino group. A loweralkyl amine is employed and the reaction is carried out by dissolving the amine in a solvent, such as a lower alcohol, preferably ethanol. The reaction is carried out at from 0° C. to the reflux temperature of the reaction mixture. However, where volatile amines are employed the reaction mixture must either be maintained at from 0° C. to room temperature or, if heating is required, the reaction must be placed in a sealed reaction vessel. It is preferred to use atmospheric pressure for the reaction, and to keep the temperature at about room temperature or less. The reaction is complete in about 1 hour to several days, with most reactions requiring stirring overnight. The product (I-A) is isolated using techniques known to those skilled in this art.

The compounds wherein Ⓐ is a saturated carbocyclic ring are prepared from the corresponding aromatic compounds by hydrogenation. The hydrogenation should take place prior to the reactions used to prepare the cyanoguanidine group, since such hydrogenation conditions might adversely affect such groups. The hydrogenation of compound II wherein Ⓐ is aromatic to compound II wherein Ⓐ is saturated is carried out under a high pressure of hydrogen, from about 1000 to 2000 psi. Usually about 1200-1400 psi is used. The reaction is carried out in a suitable solvent which will not be affected by the hydrogenation, and which will not poison or otherwise effect the catalyst. Lower alcohols are suitable, and ethanol is preferred. The reaction is generally carried out at room temperature although temperatures of from 20°-70° C. are suitable. The reaction is generally allowed to proceed overnight. Any catalyst generally suitable for reducing an aromatic ring to the corresponding saturated ring may be employed, however, it is preferred to use rhodium metal on a carbon substrate at a concentration of about 5%. The product is isolated using known techniques. Separate procedures are employed for the preparation of the other saturated rings, the 1,3-dithiane and the tetrahydro thiophene, and such procedures are outlined below.

The starting materials (II) are prepared by various procedures depending upon the value of m and n.

A procedure employed for the preparation of compounds wherein n is o involves the nitration of the imidazolyl substituted aromatic ring and reduction of the nitro group:

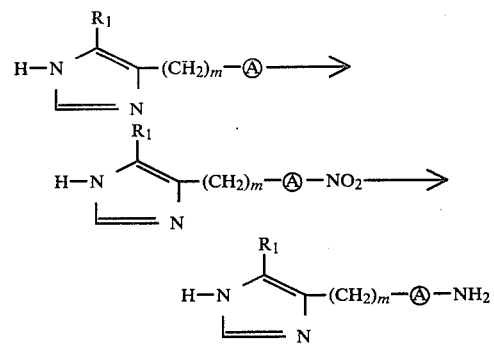

wherein $R_1$ is as defined above and Ⓐ is an aromatic ring as defined above.

The nitration is carried out using standard nitration techniques for an aromatic system such as in a mixture of concentrated nitric and sulfuric acids stirred at room temperature for from 1-5 hours. Occasionally, to direct the position of substitution of the nitration the starting material (V) has substituted on Ⓐ a halogen atom or other group which may be easily removed if desired. In the case of a halogen substituent, the removal may be accomplished during the reduction of the nitro to the amino by the appropriate selection of reagents and conditions.

Catalytic reduction is generally carried out in an alcohol solvent, or alcohol mixed with water in the presence of several equivalents of hydrochloric acid. A hydrogen atmosphere of about 50 psi is maintained and catalytic amounts of 5 to 10% palladium on carbon are present. The reaction is generally carried overnight at room temperature, although longer times and temperatures up to 70° C. may be employed. The reduction may also be performed using metal-acid combinations at 60°-100° C. wherein the metal may be iron or zinc and the acid may be acetic or a mineral acid.

Compounds wherein n is 1 are conveniently prepared from the reduction of an aromatic cyano group to an aminomethyl group. The cyano compound is prepared by displacement of an appropriately positioned halogen (Hal):

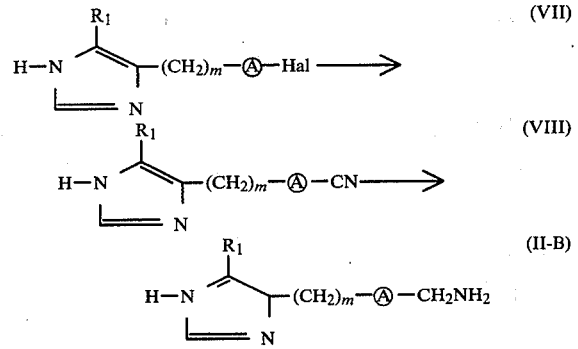

The aromatic halide (VII) is treated with a metallic cyanide such as cuprous cyanide in an appropriate high boiling solvent for 10-30 hours at from 150°-250° C. Quinoline is sufficiently high boiling and inert to the reaction conditions. The product is isolated using known techniques.

The aromatic cyanide (VIII) is reduced using hydrogenation procedures. The hydrogenation procedure previously described for the reduction of the nitro group to the amino group is suitable for the reduction of the cyano group to an aminomethyl group. The product is isolated using techniques known to those skilled in the art.

A convenient synthesis for those compounds where n is 1 to 3 involves the application of the Gabriel Synthesis. The aralkyl halide IX is treated with an alkali metal phthalimide, such as potassium phthalimide, to prepare an intermediate phthalimide compound (X) which is subsequently converted to the amine (II-C):

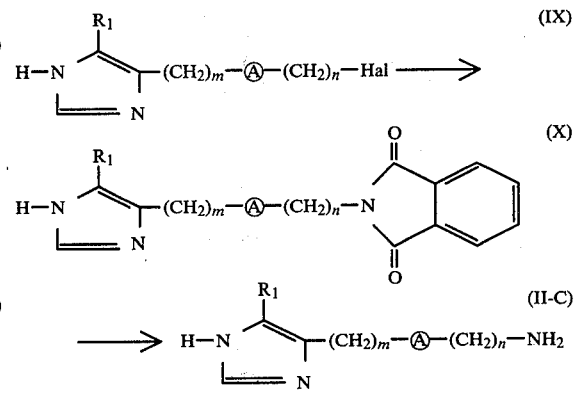

wherein $R_1$ and Ⓐ are as previously defined, n is 1 to 3 and Hal is a halide.

The displacement of the halide by the phthalimide is carried out in a solvent such as preferably dimethylformamide at a temperature of about 100° C. to 160° C., and the reaction is generally complete in about 1 to 10 hours.

The phthalimido compound (X) is treated with hydrazine followed by acid to cleave the phthalimide and leave the amino group (II-C). The reaction with hydrazine is carried out in solvent, preferably an alcohol such as ethanol and is preferably carried out at reflux temperatures and is complete in about 1 to 10 hours. The hydrazine is used in substantially equimolar quantities.

When the refluxing period with hydrazine is completed, acid is added to complete the cleavage. Preferably mineral acids such as hydrochloric are employed. The acid may be added directly to the hydrazine reaction mixture or the hydrazine reaction mixture may be evaporated and the acid, usually as an aqueous solution is added. The acid mixture is refluxed for 5 minutes to 2 hours and the product isolated by known techniques.

In most cases the reaction sequences used for preparing the starting materials are carried out sequentially. However, this is not required and in many cases where other reactions are being carried out elsewhere on the molecule, it is advantageous to start certain reaction sequences, interrupt them for other reactions, and then complete the first sequence. In the above reaction, the halo group may be displaced with the phthalimido, however, since this is a stable protecting group, other reactions, elsewhere on the molecule, may be completed before the phthalimide group is removed with base. The optimum sequence of a series of reactions will be determined by one skilled in this art with considerations of the ease of particular reactions, minimization of side reactions, and the like.

The compounds where m is 0 to 3 are prepared starting with the appropriate aromatic ketone, halogenating a carbon atom adjacent to the keto group, and cyclizing to form the imidazole ring. Slightly different starting materials are employed for those cases wherein m is 0 and where m is 1–3. For m=0:

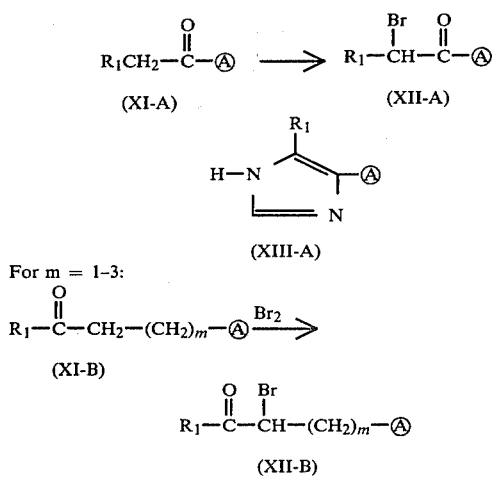

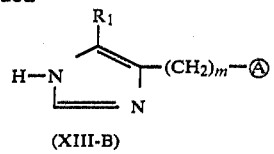

The bromination of compounds XI-A and XI-B is carried out using liquid bromine in a non-reactive solvent, such as carbon tetrachloride. The temperature is maintained at about −20° C. to room temperature and the reaction is complete in about 1–4 hours.

The bromo compound XII-A and XII-B are then dissolved in excess formamide, without any additional solvent and heated at about 150° C. to the reflux temperature of the reaction mixture. The reaction is complete in about 1–6 hours and the product XIII-A and XIII-B are isolated using techniques known to those skilled in this art.

The compounds wherein Ⓐ is a 1,3-dithiane or a tetrahydrothiophene require a somewhat different procedure starting with the appropriate 5(4)-methyl-4(5)-imidazole carboxaldehyde. In addition, the N-H group of the imidazole is protected usually with a benzyl group, to avoid side reactions.

The 4-carboxaldehyde compound wherein m=0 is prepared from the 1(3) benzyl-5-methyl-4-carbethoxy imidazole by reduction of the ester group to the hydroxy methyl group and then selective oxidation of the 1-benzyl compound to 1-benzyl 5-methyl-4-imidazole carboxaldehyde.

To prepare the 1,3-dithiane the aldehyde is treated with ethyl mercaptoacetate in the presence of a Lewis Acid such as boron trifluoride at about room temperature to prepare the bis-S-carbethoxy methyl carboxaldehyde mercaptal.

This compound is cyclized to the 4-carbethoxy 1,3-dithiane-5-one compound with sodium hydride. The reaction is carried out at room temperature in an aprotic solvent such as ethyl ether over a period of about 24 hours.

The 4-carbethoxy group is removed by hydrolytic decarboxylation and the 5-keto group converted to the amino by preparing the oxime and reducing the oxime to the amine using a metal hydride such as lithium aluminium hydride. Hydroxyl amine is used to prepare the oxime using well known reaction techniques. The reduction procedure produces cis and trans isomers. The isomers are separated using column chromatography with gradient elution and the separated isomers are cleaved of the benzyl group preparing the separate cis and trans amino starting materials wherein Ⓐ is a 1,3-dithiane:

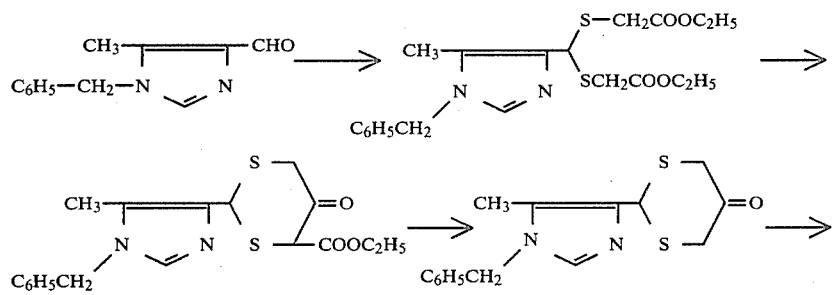

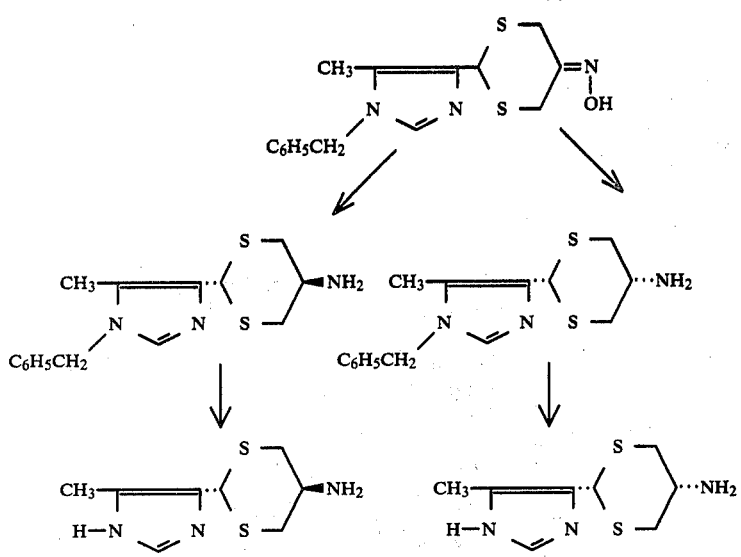

The compounds wherein Ⓐ is tetrahydrothienyl and m is 0 are prepared by converting the same imidazole-4-carboxaldehyde to the ethyl 2-propenoate with triethyl phosphonoacetate in the presence of sodium hydride and a solvent such as 1,2-dimethyloxyethane. The reaction is carried out substantially at room temperature and is complete in about 1–4 hours.

The ethyl 2-propenoate compound is reacted with ethyl mercapto acetate in the presence of n-butyl lithium in a solvent such as hexane and 1,2-dimethoxyethane. The reaction is carried out at about 50° C. and is complete in about 4–8 hours to give the ethyl 4-oxotetrahydro thiophene carboxylate compound. The ester function is removed by hydrolytic decarboxylation and the ketone converted to the oxime and then to separate cis and trans amino groups following the procedures outlined for the 1,3-dithiane compound.

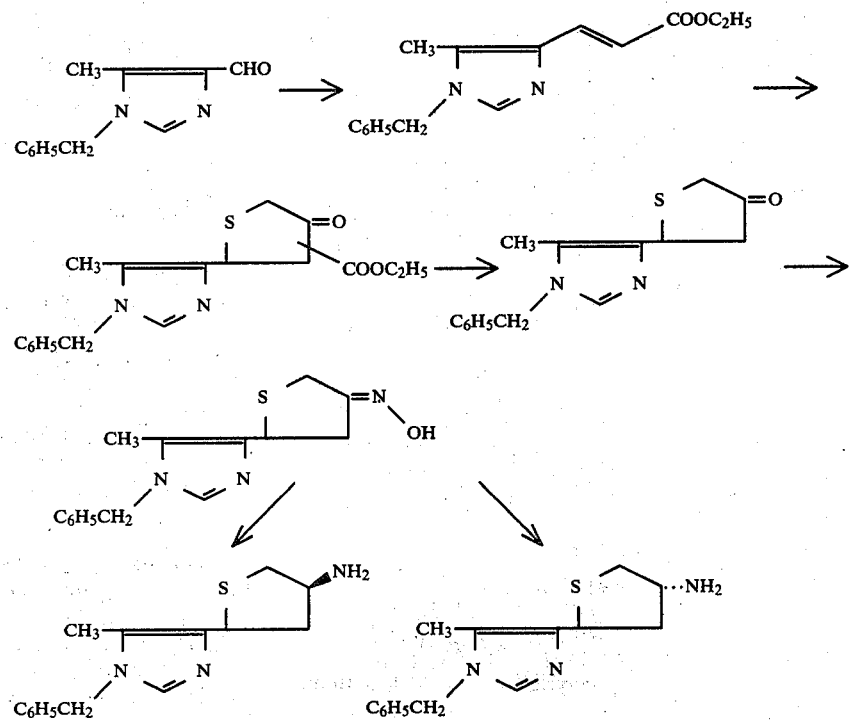

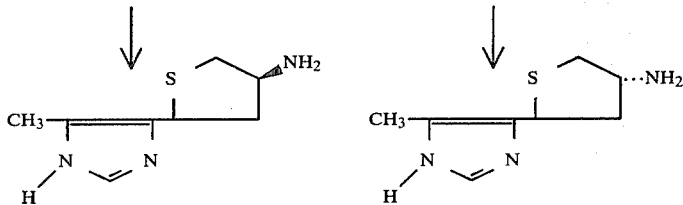

The corresponding amino starting materials for dithianyl and tetrahydrothienyl compounds in which m=1–3 are prepared by a similar sequence of reactions.

In order that this invention might be more fully understood the following examples are presented. These examples are illustrative of the manner of making this invention and are not to be construed as limitative thereof.

EXAMPLE 1

N-Cyano-N'-methyl-N''-{4-[5(4)-methyl-4(5)-imidazolyl]phenyl}guanidine

A.
N-Cyano-S-methyl-N'-{4-[5(4)-methyl-4(5)-imidazolyl]phenyl}isothiourea

To a solution of dimethyl cyanodithioimido carbonate (5.4 g., 0.037 mole) in absolute ethanol (30 ml.) is added 4(5)-methyl-5(4)-[4-aminophenyl]immidazole (5.9 g., 0.034 mole). The reaction mixture is stirred for 16 hours and 8.0 g. of precipitated N-cyano-S-methyl-N'-{4-[5(4)-methyl-4(5)-imidazolyl]phenyl}isothiourea m.p. 217°–219° C. is collected by filtration.

B.
N-Cyano-N'-methyl-N''-{4-[5(4)-methyl-4(5)-imidazolyl]phenyl}guanidine

To 30% methylamine/ethanol (by wt.) (50 ml.) is added N-cyano-S-methyl-N'-{4-[5(4)-methyl-4(5)-imidazolyl]phenyl}isothiourea (6.8 g., 0.025 mole) at ice bath temperature. The solution is gradually warmed to room temperature over 16 hours. The solvent is evaporated and the residue crystallized from methanol to give 3.7 g. of N-cyano-N'-methyl-N''-{4-[5(4)-methyl-4(5)-imidazolyl]phenyl}guanidine m.p. 243°–245° C.

Following the above procedures, using the appropriate amine starting materials, the following imidazolyl cyanoguanidines are prepared:

N-Cyano-N'-methyl-N''-{3-[5(4)-methyl-4(5)-imidazolyl]phenyl}guanidine maleate (m.p. 188°–189° C.)

N-Cyano-N'-methyl-N''-{2-[5(4)-methyl-4(5)-imidazolyl]phenyl}guanidine (m.p. 241°–244° C.)

N-Cyano-N'-methyl-N''-{4-5(4)-methyl-4(5)-imidazolyl]benzyl}guanidine (m.p. 221°–223° C.)

N-Cyano-N'-methyl-N''-{3-[5(4)-methyl-4(5)-imidazolyl]benzyl}guandine hemihydrate (m.p. 174°–177° C.)

N-Cyano-N'-methyl-N''-{2-[5(4)-methyl-4(5)-imidazolyl]benzyl}guanidine (m.p. 234°–236° C.)

N-Cyano-N'-methyl-N''-[4-{[5(4)-methyl-4(5)-imidazolyl]methyl}phenyl]guanidine (m.p. glass)

N-Cyano-N'-methyl-N''-[3-{[5(4)-methyl-4(5)-imidazolyl]methyl}phenyl]guanidine maleate (m.p. 130°–133° C.)

N-Cyano-N'-methyl-N''-[2-{[5(4)-methyl-4(5)-imidazolyl]methyl}phenyl]guanidine (m.p. 205°–207° C.)

N-Cyano-N'-methyl-N''-{cis-4-[5(4)-methyl-4(5)-imidazolyl]cyclohexyl}guanidine maleate (m.p. 174°–176° C.)

N-Cyano-N'-methyl-N'-{cis-3-[5(4)-methyl-4(5)-imidazolyl]cyclohexyl}guanidine maleate (m.p. 176°–177° C.)

N-Cyano-N'-methyl-N''-{trans-3-[5(4)-methyl-4(5)-imidazolyl]cyclohexyl}guanidine dimaleate hydrate (m.p. 167.5° C.)

N-Cyano-N'-methyl-N''-{4-chloro-3-[5(4)-methyl-4(5)-imidazolyl]phenyl}guanidine maleate (m.p,. 180°–182° C.)

N-Cyano-N'-methyl-N''-{5-[5(4)-methyl-4(5)-imidazolyl]-2-thenyl}guanidine (m.p. 203°–206° C.)

N-Cyano-N'-methyl-N''-{5-[5(4)-methyl-4(5)-imidazolyl]-2-thienyl}guanidine (m.p. 199°–200° C.)

N-Cyano-N'-methyl-N''{4-[-5(4)-methyl-4(5)-imidazolyl]-2-thienyl}guanidine maleate (m.p. 232° C. dec.)

N-Cyano-N'-methyl-N''-{cis-2[5(4)-methyl-4(5)-imidazolyl]-1,3-dithian-5-yl}guanidine (m.p. 154°–159° C.)

N-Cyano-N-methyl-N''-{trans-2[5(4)-methyl-4(5)-imidazolyl]-1,3-dithian-5-yl}guanidine N-Cyano-N'-methyl-N''-{cis-2-[5(4)-methyl-4(5)-imidazolyl]-4-tetrahydrothienyl}guanidine N-Cyano-N'-methyl-N''-{trans-2[5(4)-methyl-4(5)-imidozolyl]-4-tetrahydrothienyl}guanidine The amine starting materials for the above prepared compounds are described in the following examples:

EXAMPLE 2

4(5)-[2-aminophenyl]-5(4)-methylimidazole and 4(5)-[4-aminophenyl]-5(4)-methylimidazole A.
4(5)-[4-Nitrophenyl]-5(4)-methylimidazole To concentrated sulfuric acid (80 ml.) maintained below 10° C. is added portionwise 4(5)-phenyl- 5(4)-methylimidazole nitrate (44.0 g., 0.2 mole) obtained by crystallizing 4(5)-phenyl-5(4)-methylimidazole from 10% nitric acid. After three hours, the reaction is diluted with ice water and neutralized with sodium hydroxide. The precipitate is collected and dried in a vacuum oven affording 43.0 g. of crude product. Several recrystallizations from methanol affords 32.0 g. of 4(5)-[4-nitrophenyl]-5(4)-methylimidazole m.p. 228°–231° C.

B. 4(5)[2-Nitrophenyl]-5(4)-methylimidazole

The mother liquors from the crystallizations of 4(5)-[4-nitrophenyl]-5(4)-methylimidazole are concentrated to dryness and the residue dissolved in hot 10% nitric acid. Upon cooling to 20° C., a residual amount of 4(5)-[4-nitrophenyl]-5(4)-methylimidazole as a nitrate salt is precipitated and removed by filtration. After cooling in an ice bath, the nitrate salt of 4(5)- [2-nitrophenyl]-5(4)-methylimidazole precipitates. Neutralization of this collected salt with sodium hydroxide affords pure 4(5)-[2-Nitrophenyl]-5(4)-methylimidazole (7.0 g.) m.p. 180°–185° C.

C. 4(5)-[4-Aminophenyl]-5(4)-methylimidazole

A suspension of 4(5)-4-nitrophenyl]-5(4)-methylimidazole (12.2 g., 0.060 mole) in water (200 ml.) containing concentrated hydrochloric acid (17 ml.) and 10% Pd/C (2.0 g.) is hydrogenated in a Parr apparatus at 50 psi of hydrogen over a 2½ hour period. The catalyst is removed by filtration and the aqueous solution neutralized with sodium hydroxide. The precipitated product is filtered and dried in a vacuum oven affording 9.2 g. of 4(5)-[4-aminophenyl]-5(4)-methylimidazole m.p. 214°–217° C.

D. 4(5)-[2-Aminophenyl]-5(4)-methylimidazole

A solution of 4(5)-[2-nitrophenyl]-5(4)-methylimidazole (6.9 g., 0.034 mole) in water (100 ml.) containing concentrated hydrochloric acid (14 ml.) and 10% Pd/C (1.4 g.) is hydrogenated in a Parr apparatus under 50 psi of hydrogen over a four hour period. The catalyst is removed by filtration and the cooled solution made basic with sodium hydroxide. The precipitated product is collected and dried in a vacuum oven affording 4.3 g. of 4(5)-[2-aminophenyl]-5(4)-methylimidazole.

EXAMPLE 3

4(5)-[3-aminophenyl]-5(4)-methylimidazole

Following the procedure of Example 2C and 2D using 17.5 g. (0.0862 mole) of 5(4)-methyl-4(5)-[3-nitrophenyl]imidazole, and 2.2 g. of 10% Pd/C in 200 ml. of ethanol, there is obtained 13.1 g. of 4(5)-[3-aminophenyl]-5(4)-methylimidazole m.p. 175°–180° C.

EXAMPLE 4

4-[5(4)-Methyl-4(5)-imidazolyl]benzylamine

A. 4-[5(4)-Methyl-4(5)-imidazolyl]benzonitrile

Cuprous cyanide (15.7 g., 0.175 mole) and 4(5)-[4-chlorophenyl]-5(4)-methylimidazole (25 g., 0.13 mole) are combined and heated with quinoline (130 ml.) for 18 hours at 225° C. The reaction mixture is cooled in an ice bath, diluted with 125 ml. water and made just acid with hydrochloric acid. Hydrogen sulfide is passed through the mixture with stirring, at room temperature until all the copper sulfide is precipitated. The mixture is filtered and the solids washed with 0.5 N hydrochloric acid. The filtrate is made basic with excess sodium carbonate and extracted repeatedly with chloroform. The organic extracts are washed with brine, dried over sodium sulfate and concentrated under vacuum. The bulk of quinoline is distilled off to leave a semi-solid residue of 29 g. which is triturated with 35 ml. of chloroform and filtered to leave 13.6 g. of a product m.p. 158°–174° C. (shown by NMR to be approximately 30% nitrile contaminated with 70% starting halide). The mixture is used as is in the next step.

B. 4-[5(4)-Methyl-4(5)-imidazolyl]benzylamine

A mixture of approximately 30% 4-[5(4)-methyl-4(5)-imidazolyl]benzonitrile and 70% of 4(5)-[4-chlorophenyl]-5(4)-methylimidazole (28 g.) is dissolved in 400 ml. ethanol and 50 ml. concentrated hydrochloric acid and hydrogenated in a Parr apparatus over 10 g. of 5% Pd/C for 66 hours with additions of 3 g. of catalyst after 18 and 42 hours. The mixture is filtered and the filtrate concentrated under vacuum. The residue is made basic with sodium carbonate and the oil that separates extracted with n-butane. the organic extracts are washed with brine, dried over sodium sulfate and concentrated under vacuum. The residue (25 g.) is chromatographed on silica gel (150 g.) by elution beginning with 5% methanol in chloroform and progressing to 25% methanol in chloroform to obtain 5.4 g. of oil identified as 4-[5(4)-methyl-4(5)-imidazolyl]benzylamine by nuclear magnetic resonance.

EXAMPLE 5

3-[5(4)-Methyl-4(5)-imidazolyl]benzylamine

A. 4(5)-(3-Cyanophenyl)-5(4)-methylimidazole

2-Bromo-3'-cyanopropiophenone (32.1 g., 0.135 mole) is refluxed in formamide (180 ml.) at 190° C. for 2¼ hours under a nitrogen atmosphere. The solvent is then distilled at 80° C. at 0.6 mm. The residue is dissolved in 75 ml. of hot water, made basic with ammonium hydroxide, cooled in ice and filtered. This procedure gives 16.2 g. of tan solid. The product recrystallizes from acetonitrile, affording 4(5)-(3-cyanophenyl)-5(4)-methylimidazole m.p. 187°–193° C.

B. 3-[5(4)-Methyl-4(5)-imidazolyl]benzylamine

4(5)-(3-cyanophenyl)-5(4)-methylimidazole (5.4 g., 29.5 mmole) in ethanol (300 ml.) containing 12 N hydrochloric acid (10 ml.) is hydrogenated over 10% palladium on carbon (6.0 g.) until complete (20 hours). Water (25 ml.) is added and the catalyst is removed by filtration. The filtrate is concentrated in vacuo to a pale beige solid (6.7 g.) m.p. 282°–293° C. The free base is obtained by treating the hydrochloride salt with saturated sodium bicarbonate solution, concentrating to dryness in vacuo and extracting the residual solids with ethanol. The ethanol extract is dried, filtered and concentrated in vacuo. This gives the free base of 3-[5(4)-methyl-4(5)-imidazolyl]benzylamine as a tan solid (5.6 g.).

EXAMPLE 6

2-[5(4)-Methyl-4(5)-imidazolyl]benzylamine

A. 4(5)-[2-Chlorophenyl]-5(4)-methylimidazole

2-Bromo-2'-chloropropiophenone (26.7 g., 0.108 mole) is heated with stirring in 145 ml. formamide at 185°–192° c. for 1¾ hours. The mixture is cooled and poured into a solution of 25 ml. of concentrated ammonium hydroxide in 700 ml. water. The solid is filtered, taken up in dilute hydrochloric acid and the solution is filtered. The filtrate is made basic with ammonium hydroxide and the gray solid filtered and washed with water to obtain 15.4 g. of 4(5)-[2-chlorophenyl]-5(4)-methylimidazole m.p. 143°–148° C.

B. 2-[5(4)-Methyl-4(5)-imidazolyl]benzonitrile

Following the procedure of Example 4A, using 11.2 g. of cuprous cyanide, 15.4 g. of 4(5)-[2-chlorophenyl]-5(4)-methylimidazole and 125 ml. of quinoline, there is obtained 6.3 g. of the title compound, m.p. 142°–145° C.

C. 2-[5(4)-Methyl-4(5)-imidazolyl]benzylamine

2-[5(4)-Methyl-4(5)-imidazolyl]benzonitrile (5.5 g., 0.03 mole) is dissolved in 200 ml. ethanol containing concentrated hydrochloric acid. The solution is shaken on a Parr apparatus with 3 g. 10% Pd/C for 18 hours under an initial hydrogen pressure of 50 psi, after which time an additional 3 g. of catalyst is added and the reaction continued until hydrogen uptake ceases (24 hours). The reaction mixture is filtered and the catalyst washed with ethanol and dilute hydrochloric acid. The filtrate is concentrated under vacuum and the residue is made basic with saturated sodium carbonate. The oil that separates is extracted into n-butanol. The organic extract is washed with brine, dried over sodium sulfate and concentrated under vacuum to afford 2-[5(4)-methyl-4(5)- imidazolyl)benzylamine as a viscous amber oil, 6.3 g. solvated with n-butanol.

EXAMPLE 7

Mixture of 4(5)-[4-aminobenzyl]-5(4)-methylimidazole and 4(5)-[2-aminobenzyl]-5(4)-methylimidazole

A. Mixture of 4(5)-[4-nitrobenzyl]-5(4)-methylimidazole and 4(5)[2-nitrobenzyl]-5(4)-methylamidazole To concentrated sulfuric acid (57 ml.) cooled to −15° C. is added portionwise 4(5)-benzyl-5(4)-methylimidazole nitrate (30.2 g., 0.129 mole) obtained by crystallizing 4(5)-benzyl-5(4)-methylimidazole from the 10% nitric acid, (m.p. 148°-150° C.). After stirring for two hours, the reaction is diluted with ice water, made basic with sodium hydroxide and the precipitated product mixture collected by filtration (79.0 g.). This mixture is used in subsequent reactions, however, repeated crystalliation of this residue from absolute ethanol affords pure 4(5)-[4-nitrobenzyl]-5(4)-methylimidazole, m.p. 182°-186° C.

B. Mixture of 4(5)-[4-aminobenzyl]-5(4)-methylimidazole and 4(5)-[2-aminobenzyl]-5(4)-methylimidazole A solution of a mixture of 4(5)-[4 and 2 nitrobenzyl]-5(4)-methylimidazole (13.5 g., 0.062 mole) in water (60 ml.) and ethanol (200 ml.) containing concentrated hydrochloric acid (4.5 ml.) and 5% Pd/C (3.5 g.) is hydrogenated in Parr apparatus under 50 psi of hydrogen over a two hour period. The catalyst is removed by filtration and the ethanol under vacuum. The aqueous residue is made basic with sodium hydroxide and the produce mixture extracted into ethyl acetate, dried over sodium sulfate and evaporated to give 12.2 g. of a mixture of 4(5)-[4-aminobenzyl]-5(4)-methylimidazole and 4(5)-[2-aminobenzyl]-5(4)-methylimidazole. This mixture is utilized in subsequent reactions, however these isomers may be separated by chromatography on silica gel by gradient elution with 2-8% methanol/chloroform to give 4(5)-[4-aminobenzyl]-5(4)-methylimidazole, m.p. 146°-151° C. (from ethyl ether) and 4(5)-[2-aminobenzyl]-5(4)-methylimidazole, m.p. 151°-154° C. (from ethyl ether).

EXAMPLE 8

4(5)-[3-Aminobenzyl]-5(4)-methlimidazole

A. 4-(4-Chlorophenyl)-3-bromo-2-butanone

To a solution of 4-(4-chlorophenyl)-2-butanone (43.5 g., 0.238 mole) in carbon tetrachloride (70 ml.) cooled to −10° C. is added dropwise bromine (12.4 ml., mole). After stirring for two hours, the reacton mixture is dilted with water and extracted into chloroform. The chloroform solution is dried over sodium sulfate and evaporated in vacuo and the residue distilled under vacuum to give 34.8 g. of 4-(4-chlorophenyl)-3-bromo-2-butanone, b.p. 111°-123° C./0.4 mm/Hg.

B. 4(5)-[4-Chlorobenzyl]-5(4)-methlimidazole

A solution of 4-(4-chlorophenyl)-3-bromo-2-butanone (34.5 g., 0.132 mole) in formamide (160 ml.) is heated at 190° C. for three hours. The reaction mixture is then poured into ice water, made basic with sodium hydroxide and the gummy precipitate collected by filtration. This gum is dissolved in hot ethyl acetate, filtered through charcoal, and concentrated to a small volume. Upon cooling, the product crystallizes to give 14.6 g. of 4(5)-[4-chlorobenzyl]-5(4)-methylimidazole m.p. 165°-167° C.

C. 4(5)-[4-Chloro-3-nitrobenzyl]-5(4)-methylimidazole

4(5)-[4-Chlorobenzyl]-5(4)-methylimidazole (19.5 g., 0.094 mole) is heated with 10% nitric acid (125 ml.) until dissolved. The solution is allowed to cool and the nitrate salt is collected (24.8 g., m.p. 167°-168° C.). This salt is added in small portions to concentrated sulfuric acid cooled to 0° C. After stirring for three hours, the acid mixture is diluted with water, made basic with sodium hydroxide and extracted with chloroform which is dried over sodium sulfate and evaporated. The residue is dissolved in hot ethyl acetate and upon cooling crystalline 4(5)-[4-chloro-3-nitrobenzyl]-5(4)-methylimidazole is collected (15.3 g., m.p. 116°-119° C.).

D. 4(5)-[3-Aminobenzyl]-5(4)-methylimidazole

Following the procedure of Example 2C, using 7.5 g. of 4(5)-[4-chloro-3-nitrobenzyl]-5(4)-methylimidazole 100 ml. of water, 100 ml of ethanol, 20 ml. of concentrated hydrochloric acid and .16 g. of 10% Pd/C, there is obtained 5.2 g. of 4(5)-[3-aminobenzyl]-5(4)-methylimidazole m.p. 149°-152° C.

EXAMPLE 9

Cis-4(5)-[4-aminocyclohexyl]-5(4)-methylimidazole

A solution of 4(5)-[4-aminophenyl]-5(4)-methylimidazole (6.7 g., 0.039 mole) in 5% hydrochloric acid (250 ml.) and containing 5% Rh/C (3.0 g.) is hydrogenated at room temperature in a pressurized bomb at 1200 psi of hydrogen over a 24 period. The catalyst is filtered and the filtrate neutralized with sodium hydroxide. The product is extracted into ethyl acetate, dried over sodium sulfate and evaporated to 6.0 g. of cis-4(5)-[4-aminocyclohexyl]-5(4)-methylimidazole.

EXAMPLE 10

Cis and trans 3-[5(4)-methyl-4(5)-imidazolyl)]cyclohexylamine

3-[5(4)-Methyl-4(5)-imidazolyl)]aniline (14.2 g. 0.082 mole) is catalytically reduced in 500 ml. of 5% HCl over 7 g. 5% Rh/C at 1200 psi. The reaction mixture is filtered and concentrated to a small volume under vacuum. The residue is made basic with saturated sodium carbonate and the oil that separates is extracted with n-butanol. The organic extracts are washed with brine, dried over sodium sulfate and concentrated under vacuum to obtain 15.6 g. of a mixture of cis and trans 3-[5(4)-methyl-4(5)-imidazolyl)]cyclohexylamine as a viscous amber oil.

EXAMPLE 11

4-Chloro-3-[5(4)-methyl-4(5)-imidazolyl)]aniline

A. 2-Bromo-2'-chloro-5'-nitropropiophenone

2'-Chloro-5'-nitropropiophenone (30 g., 0.140 mole) is dissolved in 100 ml. carbon tetrachloride containing 1 drop of glacial acetic acid. Bromine (22.4 g., 0.140 mole) dissolved in 20 ml. of carbon tetrachloride is added maintaining a reaction temperature 15°–20° over 40 minutes after which the reaction is concentrated under vacuum. The residual oil is taken up in hexane (100 ml.) and thr product which crystallizes is filtered to obtain 38.8 g. of 2-bromo-2'-chloro-5'-nitropropiophenone m.p. 81.5°–83.5° C.

B. 4(5)-[2-Chloro-5-nitrophenyl]-5(4)-methylimidazole

2-Bromo-2'-chloro-5'-nitropropiophenone (35.2 g., 0.1205 mole) is heated with stirring in 200 ml. formamide at 185°–195° for 1¾ hours. The reaction mixture is worked up as in Example 8B to afford 4(5)-[2-chloro-5-nitrophenyl)-5(4)-methylimidazole]m.p. 234°–239° C. (dec).

C. 4-Chloro-3-[5(4)-methyl-4(5)-imidazolyl)]aniline

To a suspension of 10.3% of powdered iron in water (75 ml.) warmed to 60° is added dropwise a solution of 4(5)-[2-chloro-5-nitrophenyl]-5(4)-methylimidazole (5.2 g., 0.019 mole) in glacial acetic acid (14 ml.) maintaining a temperature of 60° C. After ½ hour the mixture is heated on a steam bath for four additional hours. It is cooled and diluted with n-butanol (75 ml.) and the liquid decanted from the iron residues. The n-butanol-water layers are treated with solid sodium bicarbonate and extracted with methylene chloride-n-butanol. The organic layer is washed with saturated sodium carbonate, and saturated sodium chloride, dried over sodium sulfate and evaporated to dryness in vacuo. The residue is dissolved in 1:1 tetrahydrofuran/ethylacetate, filtered and evaporated to give 4.4 g. of 4-chloro-3-[5(4)-methyl-4(5)-imidazolyl]aniline as a glass.

EXAMPLE 12

4(5)-[5-Aminomethyl-2-thienyl]-5(4)-methylimidazole

A. 2-Phthalimidomethyl-5-propionylthiophene

2-Phthalimidomethylthiophene (2.43 g., 10 mole) and propionic anhydride (1.55 g., 12 moles) are heated together on a steam bath. Then 85% phosphoric acid (0.1 ml.) is added and the mixture is heated for 3 hours on the steam bath. The mixture is cooled in ice and water (5 ml.) is added to precipitate the product. The solid is filtered, dissolved in methylene chloride, washed with water, dried over anhydrous sodium sulfate, filtered and concentrated in vacuo to give 2-phthalimidomethyl-5-propionylthiophene as a light tan solid (2.5 g.), m.p. 104°–106° C.

B. 5-(2-Bromopropionyl)-2-(phthalimidomethyl)thiophene

2-Phthalimidomethyl-5-propionylthiophene (39.3 g., 0.13 mole) is dissolved in methylene chloride 300 ml.) and bromine (20.8 g., 0.13 mole) is added dropwise with stirring over ¾ hours at room temperature. The solution is partially evaporated in vacuo to remove the hydrogen bromide. Then it is washed with saturated sodium carbonate solution and with water, dried over anhydrous sodium sulfate, filtered and concentrated in vacuo. This affords 5-(2-bromopropionyl)-2-(phthalimidomethyl) thiophene as a pale beige solid (46.7 g.), m.p. 127°–130° C.

C. 5(4)-Methyl-4(5)-[5-phthalimidomethyl-2-thienyl]imidazole 5-(2-Bromopropionyl)-2-phthalimidomethylthiophene (46.7 g., 0.123 mole) is heated in formamide (230 ml.) at 185°–190° C. for 1½ hours under a nitrogen atmosphere. The solution is cooled and is poured into water (400 ml.) and made basic with ammonium hydroxide. After filtration, the collected brown solid (33.9 g.) is recrystallized several times from isopropanol and 5(4)-methyl-4(5)-[5-phthalimidomethyl-2-thienyl]imidazole is obtained as a yellow-brown solid (18.4 g.) m.p. 195°–203° C.

D. 4(5)-[5-Aminomethyl-2-thienyl]-5(4)-methylimidazole

5(4)-Methyl-4(5)-[5-phthalimidomethyl-2-thienyl-]imidazole (20.3 g., 63 moles) is suspended in methanol (400 ml.) and hydrazine hydrate (3.5 g., 70 moles) is added. The mixture is stirred at reflux for 1¼ hours and is filtered. The filtrate is concentrated in vacuo to a brown gum. The gum is dissolved in water (50 ml.) and is acidified with 6 N hydrochloric acid (20 ml.). The acid solution is heated for 10 minutes on a steam bath and is cooled in ice and filtered. The filtrate is made basic with sodium carbonate and is extracted several times with methylene chloride. The extracts are dried over anhydrous sodium sulfate, filtered and concentrated in vacuo. This affords 12.4 g. of 4(5)-[5-aminomethyl-2-thienyl]-5(4)-methylimidazole as a light beige solid.

EXAMPLE 13

4(5)-[5-Amino-2-thienyl]-5(4)-methylimidazole

A. 5(4)-Methyl-4(5)-[2-thienyl]imidazole 2-(2-Bromopropionyl) thiophene (104.7 g., 0.48 mole) is refluxed in formamide (450 ml.) at 185° C. for 3 hours under a nitrogen atmosphere. The product crystallizes upon cooling and is filtered. The solid is dissolved in warm water (400 ml.). This solution is made basic with saturated sodium bicarbonate and is filtered. A light gray solid (47.6 g.) is obtained, m.p. 171°–172° C. The product is recrystallized from acetonitrile or ethanol/water (2:5) affording 5(4)-methyl-4(5)-[2-thienyl]imidazole m.p. 172°–173° C.

B. 5(4)-Methyl-4(5)-[5-nitro-2-thienyl]imidazole

5(4)-Methyl-4(5)-[2-thienyl]imidazole (1.0 g., 0.006 moles) is added to 10% nitric acid (15 ml.) and the suspension is heated for 42 hours at steam bath temperature. A solution forms and a yellow solid separates. The mixture is made basic with ammonium hydroxide and is filtered. The product is an orange solid (0.52 g.) which is recrystallized from nitromethane, m.p. 270° C. (with slow decomposition).

C. 4(5)-[5-Amino-2-thienyl]-5(4)-methylimidazole

5(4)-Methyl-4(5)-[5-nitro-2-thienyl]imidazole (5.23 g., 0.025 moles) in ethanol (250 ml.) is hydrogenated over 10% palladium on carbon (10 g.). When the required amount of hydrogen is absorbed the mixture is filtered under a nitrogen atmosphere. The filtrate is concentrated in vacuo to about 50 ml. and this amine solution is used in subsequent steps without further purification.

EXAMPLE 14

4(5)-[4-Amino-2-thienyl]-5(4)-methylimidazole

A. 2-(2-Bromopropionyl)-4-nitrothiophene

Following the procedure of Example 12B, using 9.26 g. of 2-propionyl-4-nitrothiophene and 7.99 g. of bromine in 100 ml. of methylene chloride, there is obtained 13.0 g. of product m.p. 79°–82° C. which is recrystallized from ethanol affording 2-(2-bromopropionyl)-4-nitrothiophene m.p. 82.5°–83° C.

B. 5(4)-Methyl-4(5)-[4-nitro-2-thienyl]imidazole

Following the procedure of Example 12C, using 6.6 g. of 2-(2-bromopropionyl)-4-nitrothiophene in 35 ml. of formamide, there is obtained 3.3 g. of product m.p. 190°–205° C. which recrystallizes from ethanol affording 5(4)-methyl-4(5)-[4-nitro-2-thienyl]imidazole m.p. 238°–240° C.

C. 4(5)-[4-Amino-2-thienyl]-5(4)-methylimidazole

Following the procedure of Example 13C using 10.5 g. of 5(4)-methyl-4(5)-[4-nitro-2-thienyl]imidazole and 5.0 g. of 10% palladium on carbon in 50 ml. of ethanol, there is obtained 4(5)-[4-amino-2-thienyl]-5(4)-methylimidazole as a pale yellow solution which is used in subsequent steps without further purification.

EXAMPLE 15

Cis-2-[5(4)-methyl-4(5)-imidazolyl]-5-amino-1,3-dithiane

A. Mixture of Ethyl (1-and 3-benzyl)-5-methyl-4-imidazole carboxylates

A mixture of ethyl 5(4)-methyl-4(5)-imidazole carboxylate (77.0 g., 0.5 mole) and 50% sodium hydride in mineral oil (25.0 g., 0.52 mole) in dry dimethylformamide (700 ml.) is heated at 90° C. for 1 hour. Benzylchloride (60 ml., 0.51 mole) is added dropwise at this temperature. When the addition is complete, the mixture is heated at 100° C. for 2 additional hours and then cooled, filtered and the solvent evaporated. This residue is dissolved in methylene chloride and the product extracted into 10% hydrochloric acid. Upon neutralization with base, the product is extracted into methylene chloride, dried and evaporated to give 107 gm. of a crude isomeric mixture of ethyl (1- and 3-benzyl)-5-methyl-4-imidazole carboxylates.

B. Mixture of 1- and 3-benzyl-5-methyl-4-hydroxymethyl imidazoles

To a suspension of lithium aluminum hydride (152 g., 0.4 mole) in dry tetrahydrofuran (650 ml.) is added dropwise a solution of the mixture of ethyl (1- and 3-benzyl)-5-methyl-4-imidazole carboxylates (94 gm., 0.385 mole) in dry tetrahydrofuran (100 ml.). The addition is exothermic. After the addition the reaction mixture is maintained at reflux for 2 hours and then carefully quenched with 5% sodium hydroxide (67 ml.). The resulting salts are filtered from the hot solution and the filtrate is concentrated to a small volume and diluted with diethyl ether. The precipitated isomeric product mixture (42 g.) is collected and used as is. By a careful crystallization of this mixture from tetrahydrofuran, pure 1-benzyl-5-methyl-4-hydroxymethyl imidazole can be obtained, m.p. 176°–180° C.

C. 1-Benzyl-5-methyl-4-imidazole carboxaldehyde

To a solution of a mixture of 1- and 3-benzyl-5-methyl-4-hydroxymethyl imidazole (25.4 g., 0.126 mole) in chloroform (590 ml.) is added activated manganese dioxide (44 g.). The reaction mixture is refluxed for five hours. The manganese dioxide is removed by filtration of the hot solution and washed with hot chloroform. The combined filtrates are evaporated. The residue is digested in a small volume of methylene chloride, cooled and unreacted pure 3-benzyl-5-methyl-4-hydroxymethylimidazole is collected, m.p. 155°–158° C. (9.5 g.). Upon dilution of the filtrate with ethyl ether, the product 1-benzyl-5-methyl-4-imidazole carboxaldehyde crystallizes out to give 9.4 g., m.p. 107°–110° C.

D. 3-[bis-(ethoxycarbonylmethylthio)methyl]-1-benzyl-5-methyl-4-imidazole

To a solution of 1-benzyl-5-methyl-4-imidazole carboxaldehyde (20 g., 0.1 mole) in chloroform (300 ml.) is added ethyl mercaptoacetate (22 ml., 0.2 mole) and boron trifluoride etherate (20 ml.). The solution is stirred at ambient temperature for 48 hours. The solution is then washed with saturated sodium carbonate, dried and evaporated to give an oily product (41 g.) of 3-[bis-(ethoxycarbonylmethylthio)methyl]-1-benzyl-5-methyl-4-imidazole which is used as is in subsequent steps.

E. 2-(1-Benzyl-5-methyl-4-imidazolyl)-4-carbethoxy-1,3-dithian-5-one

To a suspension of 50% sodium hydride in mineral oil (10 g., 0.21 mole) in dry diethyl ether (250 ml.) under a nitrogen atmosphere is added dropwise at ambient temperature a solution of 3-[bis-(ethoxycarbonylmethylthio)methyl]-1-benzyl-5-methyl-4-imidazole (41 g., 0.097 mole) in diethyl ether (100 ml.). The reaction is stirred at ambient temperature for 24 hours. The precipitated brown salt is collected by filtration. The salt is dissolved in water and neutralized with 10% hydrochloric acid. The product is extracted into methylene chloride, dried and evaporated to give a viscous brown oil (30 g.) 2-(1-benzyl-5-methyl-4-imidazolyl)-4-carbethoxy-1,3-dithian-5-one. The product is used as is in subsequent steps.

F. 2-(Benzyl-5-methyl-4-imidazolyl)-1,3-dithian-5-one

A mixture of 2-(1-benzyl-5-methyl-4-imidazolyl)-4-carbethoxy-1,3-dithian-5-one (15.5 g., 0.041 mole) in water (40 ml.) containing concentrated sulfuric acid (3.0 ml.) is heated at 100° C. for 4–5 hours. The mixture is cooled, diluted with 10% hydrochloric acid, washed with diethyl ether and filtered through a charcoal pad. The filtrate is made basic with sodium carbonate solution and extracted into methylene chloride. The solvent is dried and evaporated to give a dark brown oil (11.2 g.), 2-(1-benzyl-5-methyl-4-imidazolyl)-1,3-dithian-5-one, which is used as is in subsequent steps.

G. 2-(1-Benzyl-5-methyl-4-imidazolyl)-1,3-dithian-5-one oxime

To a solution of 2-(1-benzyl-5-methyl-4-imidazolyl)-1,3-dithian-5-one (11.2 g., 0.0368 mole) in methanol (50 ml.) and water (20 ml.) is added sodium acetate (3.1 g.) and hydroxylamine hydrochloride (2.6 g., 0.037 mole). The reaction is stirred at ambient temperature for 5 hours. The mixture is diluted with chloroform, washed with water, dried and evaporated to give a solid crude product (11.1 g.), 2-(1-benzyl-5-methyl-4-imidazolyl)-1,3-dithian-5-one oxime, which is used as is in the following steps.

H. Cis and Trans 2-(1-benzyl-5-methyl-4-imidazolyl)-5-amino-1,3-dithiane

To a suspension of lithium aluminum hydride (2.9 g., 0.076 mole) in dry tetrahydrofuran (120 ml.) under a nitrogen atmosphere is added dropwise a solution of 2-(1-benzyl-5-methyl-4-imidazolyl)-1,3-dithian-5-one oxime (21.3 g., 0.0668 mole) in dry tetrahydrofuran (130 ml.). After heating at 70° C. for one hour, water (40 ml.) is added cautiously and the mixture is filtered hot. The solvent is evaporated and the residue is chased with ethanol to remove traces of water to give a viscous oil (17.0 g.). Careful chromatography on silica gel by gradient elution with 2–6% methanol/chloroform affords 2.2 g. of the trans isomer and 7.3 g. of the cis isomer as viscous semi-solids.

I. Cis-2-[5(4)-methyl-4(5)-imidazolyl]-5-amino-1,3-dithiane

To a partial suspension of cis-2-(1-benzyl-5-methyl-4-imidazolyl-5-amino-1,3-dithiane (4.3 g., 14.1 mole) in dry dimethoxyethane (20 ml.) is added liquid ammonia (80 ml.). Sodium pellets (0.9 g., 39 mole) are then added portionwise over a one hour period. The reaction is stirred for one hour and quenched with sodium ammonium chloride (3.0 g.). After the ammonia evaporates, the residue is diluted with diethyl ether and the solid collected by filtration. This solid is dissolved in aqueous sodium carbonate and the product extracted into methylene chloride/ethanol, dried and evaporated to give cis-2-[5(4)-methyl-4(5)-imidazolyl]-5-amino-1,3-dithiane as a viscous solid.

EXAMPLE 16

Trans-2-[5(4)-methyl-4(5)-imidazolyl]-5-amino-1,3-dithiane

Following the procedure of Example 15 part I using as starting material the trans isomer obtained in Example 15, part H, there is obtained trans-2-[5(4)-methyl-4(5)-imidazolyl]-5-amino-1,3-dithiane.

EXAMPLE 17

Cis-2-[5(4)-methyl-4(5)-imidiazolyl]-4-aminotetrahydrothiophene

A. Ethyl 3-(1-benzyl-5-methyl-4-imidazolyl)-2-propenoate

A suspension of 50% sodium hydride in mineral oil (1.03 g., 0.0215 mole) in dry 1,2-dimethoxyethane (50 ml.) is cooled to 10° C. and triethyl phosphonoacetate (4.82 g., 0.0215 mole) is added dropwise over 5 minutes under nitrogen atmosphere. The mixture is stirred at 10° to 20° C. for ¾ hour. Then 1-benzyl-5-methyl-4-imidazolecarboxaldehyde (4.1 g., 0.02 mole) is added over 5 minutes and the mixture is stirred at room temperature for 1¾ hours. The reaction mixture is cooled in an ice bath and is diluted with 100 ml. of ether and 50 ml. of ice water. The organic layer is separated and extracted with cold 3 N hydrochloric acid (50 ml.). The acidic extract is neutralized with sodium bicarbonate and the product is extracted into ether. The ether extract is dried over anhydrous sodium sulfate, filtered and concentrated in vacuo. The product is an amber oil which solidifies to a yellow solid (5.4 g.). The crude ethyl 3-(1-benzyl-5-methyl-4-imidazolyl)-2-propenoate melts at 169°–180° C.

B. Ethyl 2-[1-benzyl-5-methyl-4-imidazolyl]-4-oxotetrahydrothiophene-5-(and/or 3)-carboxylate A solution of ethyl mercaptoacetate (7.45 g., 0.062 mole) in 59 ml. of dry 1,2-dimethoxyethane is cooled to 5° C. and n-butyl lithium (41.3 ml., 0.062 mole) in hexane is added dropwise over ½ hour under a nitrogen atmosphere. To this solution is added ethyl 3-(1-benzyl-5-methyl-4-imidazolyl)-2-propenoate (13.0 g., 0.0514 mole) in 50 ml. of 1,2-dimethoxyethane at 10° C. The mixture is stirred at 50°–55° C. for 6 hours and is left at room temperature overnight. The reaction mixture is cooled in ice and is diluted with 300 ml. of ether and filtered. The solid is dissolved in 100 ml. of water and is acidified with dilute hydrochloric acid. The mixture is made basic with sodium bicarbonate and is extracted with a mixture of chloroform and methylene chloride. The combined extracts are dried over anhydrous sodium sulfate, filtered and concentrated in vacuo. The product ethyl 2-[1-benzyl-5-methyl-4-imidazolyl]-4-oxotetrahydrothiophene-5-(and/or 3)-carboxylate is obtained as a brown viscous liquid (12.6 g.).

C. 2-(1-Benzyl-5-methyl-4-imidazolyl)-4-oxotetrahydrothiophene

Ethyl 2-(1-benzyl-5-methyl-4-imidazolyl)-4-oxotetrahydrothiophene-5(and/or 3)-carboxylate (12.6 g., 0.037 mole) is dissolved in 20 ml. of water containing concentrated sulfuric acid (1.11 ml., 0.02 mole) and the solution is refluxed for 3¼ hours. The reaction mixture is diluted with 50 ml. of water and is washed with ether. The aqueous layer is made basic with sodium carbonate and the oil which separates is extracted into chloroform. The extract is washed with water, dried over anhydrous sodium sulfate, filtered and concentrated in vacuo. The product 2-(1-benzyl-5-methyl-4-imidazolyl)-4-oxotetrahydrothiophene is isolated a brown gum (7.8 g.).

D. 2-(1-Benzyl-5-methyl-4-imidazolyl)-4-oxotetrahydrothiophene oxime 2-(1-Benzyl-5-methyl-4-imidazolyl)-4-oxotetrahydrothiophene (0.14 g., 0.5 mole) is dissolved in 1 ml. of ethanol and 1 ml. of water is added. Then hydroxyamine hydrochloride (38 mg., 0.55 mole) and sodium acetate (45 mg., 0.55 mole) are added. The mixture is stirred at room temperature overnight. The reaction mixture is concentrated in vacuo. The residue is triturated with chloroform and the mixture is filtered. The chloroform extract is dried over anhydrous sodium sulfate, filtered and concentrated in vacuo. The crude oxime, 2-(1-benzyl-5-methyl-4-imidazolyl)-4-oxotetrahydrothiophene oxime, is a brown viscous oil (0.15 g.).

E. Cis and Trans 2-(1-benzyl-5-methyl-4-imidazolyl)-4-amino tetrahydrothiophene The procedure of Example 15 part H is followed using 2-(1-benzyl-5-methyl-4-imidazolyl-4-oxotetrahydrothiophene oxime as starting material. Column chromatography on the mixture of reduction products affords separate cis and trans products.

F. Cis-2-[5(4)-methyl-4(5)-imidazolyl]-4-amino tetrahydrothiophene

Following the procedure of Example 15 part I using the cis isomer obtained from Example 17 part E there is obtained cis-2-[5(4)-methyl-4(5)-imidazolyl]-4-aminotetrahydrothiophene.

EXAMPLE 18

Trans-2-[5(4)-methyl-4(5)-imidazolyl]-4-amino tetrahydrothiophene

Following the procedure of Example 15 part I using the trans isomer obtained from Example 17 part E, there is obtained trans-2-[5(4)-methyl-4(5)-imidazolyl]-4-aminotetrahydrothiophene.

What is claimed is:

1. A compound having the formula:

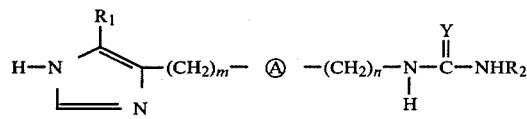

wherein
$R_1$ is hydrogen or methyl;
$R_2$ is loweralkyl;
m and n are independently 0 to 3;
Ⓐ is a cyclic bivalent radical selected from phenylene, cyclohexylene, thienylene, tetrahydrothienylene, and 1,3-dithianylene, which may optionally be substituted with a halogen, and
Y is oxygen, sulfur, $=NR_3$ or $=CHR_4$ wherein:
$R_3$ is hydrogen, cyano, loweralkyl, phenyl, loweralkylsulfonyl or phenylsulfonyl; and
$R_4$ is nitro, phenylsulfonyl or loweralkylsulfonyl.

2. The compound of claim 1 wherein Y is nitromethylidene.

3. The compound of claim 1 wherein Y is cyanoimino.

4. The compound of claim 3 wherein:
$R_1$ is methyl;
$R_2$ is methyl; and
m and n are independently 0 or 1.

5. The compound of claim 4 wherein Ⓐ is phenylene or cyclohexylene which may be optionally substituted with chlorine.

6. The compound of claim 5 wherein Ⓐ is 1,3-phenylene, chloro-1,3-phenylene, 1,3-cyclohexylene, or 1,2-phenylene.

7. The compound of claim 6 which is N-cyano-N'-methyl-N''-{3-[5(4)-methyl-4(5)-imidazolyl]phenyl}-guanidine.

8. The compound of claim 6 which is N-cyano-N'-methyl-N''-{4-chloro-3-[5(4)-methyl-4(5)-imidazolyl]phenyl}guanidine.

9. The compound of claim 6 which is N-cyano-N'-methyl-N''-{cis-3-[5(4)-methyl-4(5)-imidazolyl]cyclohexyl}guanidine.

10. The compound of claim 6 which is N-cyano-N'-methyl-N''-{2-[5(4)-methyl-4(5)-imidazolyl]benzyl}-guanidine.

11. A method for the treatment of excess gastric acid secretions which comprises administering to a mammal with such excess gastric acid secretions, an effective amount of a compound of claim 1.

12. A composition useful for the treatment of excess gastric acid secretions which comprises an inert carrier and an effective amount of a compound of claim 1.

* * * * *